(12) United States Patent
Boyd et al.

(10) Patent No.: US 9,161,890 B2
(45) Date of Patent: Oct. 20, 2015

(54) MULTILAYER FILMS FOR DELIVERY OF FLAVOR

(75) Inventors: Thomas Boyd, Metuchen, NJ (US); Ben Gu, East Brunswick, NJ (US); Leonora Leigh, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/806,535

(22) PCT Filed: Jun. 30, 2010

(86) PCT No.: PCT/US2010/040507
§ 371 (c)(1),
(2), (4) Date: Dec. 21, 2012

(87) PCT Pub. No.: WO2012/002945
PCT Pub. Date: Jan. 5, 2012

(65) Prior Publication Data
US 2013/0101652 A1    Apr. 25, 2013

(51) Int. Cl.
*A61K 8/02* (2006.01)
*A61K 8/73* (2006.01)
*A61K 8/81* (2006.01)
*A61Q 11/00* (2006.01)

(52) U.S. Cl.
CPC .............. *A61K 8/0233* (2013.01); *A61K 8/02* (2013.01); *A61K 8/731* (2013.01); *A61K 8/8135* (2013.01); *A61Q 11/00* (2013.01); *A61K 2800/242* (2013.01); *A61K 2800/244* (2013.01)

(58) Field of Classification Search
None
See application file for complete search history.

(56) References Cited

U.S. PATENT DOCUMENTS

| | | | |
|---|---|---|---|
| 3,957,964 A | 5/1976 | Grimm, III | |
| 4,423,030 A * | 12/1983 | Hayes et al. | 424/58 |
| 4,515,769 A * | 5/1985 | Merritt et al. | 424/49 |
| 4,820,506 A | 4/1989 | Kleinberg et al. | |
| 4,839,157 A | 6/1989 | Mei-King Ng et al. | |
| 4,900,552 A | 2/1990 | Sanvordeker et al. | |
| 5,047,244 A | 9/1991 | Sanvordeker et al. | |
| 5,695,746 A | 12/1997 | Garlick, Jr. et al. | |
| 5,700,478 A * | 12/1997 | Biegajski et al. | 424/434 |
| 5,948,430 A | 9/1999 | Zerbe et al. | |
| 6,231,957 B1 | 5/2001 | Zerbe et al. | |
| 6,241,974 B1 | 6/2001 | White, Jr. et al. | |
| 6,315,986 B1 | 11/2001 | Wong et al. | |
| 6,585,997 B2 | 7/2003 | Moro et al. | |
| 6,596,298 B2 | 7/2003 | Leung et al. | |
| 6,669,929 B1 | 12/2003 | Boyd et al. | |
| 6,709,671 B2 | 3/2004 | Zerbe et al. | |
| 7,132,113 B2 | 11/2006 | Zerbe et al. | |
| 7,220,404 B2 | 5/2007 | Morgan et al. | |
| 2002/0048553 A1 | 4/2002 | Baumgartner | |
| 2004/0126332 A1 | 7/2004 | Boyd et al. | |
| 2004/0136924 A1 * | 7/2004 | Boyd et al. | 424/48 |
| 2005/0106112 A1 * | 5/2005 | Boyd et al. | 424/49 |
| 2006/0204613 A1 * | 9/2006 | Castro et al. | 426/3 |
| 2006/0286200 A1 * | 12/2006 | Castro et al. | 426/3 |
| 2007/0148213 A1 | 6/2007 | Ibrahim et al. | |
| 2008/0160056 A1 | 7/2008 | Boyd et al. | |
| 2009/0165371 A1 | 7/2009 | Chevalier et al. | |
| 2010/0112050 A1 | 5/2010 | Ryoo et al. | |

FOREIGN PATENT DOCUMENTS

| | | |
|---|---|---|
| JP | 2010-138125 | 6/2010 |
| WO | WO 02/092038 | 11/2002 |
| WO | WO 2005/058265 | 6/2005 |
| WO | WO 2010/112050 | 10/2010 |
| WO | WO 2010/114551 | 10/2010 |

OTHER PUBLICATIONS

International Search Report and the Written Opinion issued in PCT/US2010/040507 mailed Jun. 28, 2011.

* cited by examiner

*Primary Examiner* — Robert A Wax
*Assistant Examiner* — Olga V Tcherkasskaya (57) ABSTRACT

An oral care composition having enhanced flavor release comprising an orally acceptable carrier containing a first flavor and a multilayer film for extended or delayed flavor release, the multilayer film including at least a center layer containing a second flavor, the center layer positioned between two outer surface layers, each surface layer including a release modulating agent, the first and second flavor being the same or different. The film is adapted to adhere to an oral cavity surface and the outer surface layers may comprise a mucoadhesive polymer, e.g. carboxy polymethylene, polycarbophil or polyvinyl pyrrolidone, and a film forming polymer, eg. hydroxypropylmethyl cellulose (HPMC). Suitable release modulating agents include HPMC and polyvinyl acetate. The carrier may be a toothpaste or mouthwash.

13 Claims, 4 Drawing Sheets

Binding of film without Carbopol 971P

FIGURE 3(a)

Binding of film with Carbopol 971P

FIGURE 3(b)

Figure 4(a). Example of ABC structure

Figure 4(b). Example of ABC Output

MULTILAYER FILMS FOR DELIVERY OF FLAVOR

BACKGROUND

This application relates to oral care compositions, and more particularly to compositions comprising a multilayer film entrained in an orally acceptable carrier, in which the multilayer film includes a flavor which can be released in prolonged or delayed manner after the application of the oral composition is completed. Such compositions include, for example, dentifrices, mouthwashes and/or oral rinses.

Oral care products usually contain three major components, namely, flavor, vehicle and functional agents. Flavor is an essential component in both dentifrices and oral rinses and is one of the most important features of an oral care product. Flavor also plays a critical role in the success of an oral care product. Good flavor not only enhances product acceptability, but also attracts consumers to buy the product again. Flavor provides not only a sensation of taste on the tongue and of odor in the olfactory center of the nose, but also a key signal which, when perceived by the brain, becomes closely linked to product characteristics and performance to influence the perceptions of the consumer.

The aesthetic appeal of compositions is also important, and can have significant effects on consumer acceptance and usage. Aesthetic effects have been acknowledged to play an important role in consumer acceptance of many products. Although such products have met with consumer approval, the art seeks to further improve the aesthetic effects as well as the cosmetic and therapeutic benefits of these products. Indeed, many such compositions known in the art are deficient in one or more attributes.

Water-soluble films for oral administration of therapeutic agents are well known in the art. It is also known in the art to use such films for administering a breath freshening agent, e.g., menthol. The known films for administering breath freshening agents and/or active pharmaceutical agents are generally comprised of at least one water-soluble polymer suitable for human consumption and at least one compound that enhances the wettability of the water-soluble polymer, typically selected from polyalcohols, surfactants and plasticizers. For example, U.S. Pat. No. 5,948,430, the disclosure of which is incorporated by reference herein in its entirety, describes a monolayer film that can be adhered to the oral cavity to release a pharmaceutically or cosmetically active ingredient, wherein the film comprises at least one water-soluble polymer; at least one member selected from the group consisting of a polyalcohol, a surfactant and a plasticizer; at least one cosmetic or pharmaceutically active ingredient; and a flavoring agent.

U.S. Pat. No. 5,700,478, the disclosure of which is incorporated by reference herein in its entirety, describes a laminated device for controlled release of a substance within a mucosa-lined body cavity including a water-soluble adhesive layer comprised of a water-soluble polymer and a water-soluble plasticizer, and a water-soluble polymer layer. This patent teaches a multiple layer laminate that dissolves relatively slowly for controlled or sustained release of a substance.

U.S. Pat. No. 4,900,552, the disclosure of which is incorporated by reference herein in its entirety, describes a trilaminate film suitable for prolonged and sustained delivery of an active ingredient in a buccal cavity. The trilaminate includes a hydratable muco-adhesive base layer; a non-adhesive reservoir layer; and a water-impermeable barrier sandwiched between and bonded to the base layer and the reservoir layer. This patent discloses slowly disintegrating films for prolonged or sustained release of a substance.

U.S. Pat. No. 5,047,244, the disclosure of which is incorporated by reference herein in its entirety, discloses a therapeutic dosage form comprising an anhydrous but hydratable monolithic polymer matrix that contains amorphous fumed silica as well as a therapeutic agent, and a water-insoluble barrier layer secured to the polymer matrix and defining a non-adhesive face. This patent does not disclose rapidly disintegrating films, but instead contemplates compositions that are capable of providing improved availability of therapeutic agents from a controlled release muco-adhesive carrier system.

U.S. Pat. No. 6,669,929, and U.S. Pat. No. 7,132,113, the disclosures of each of which are incorporated by reference herein in their entirety, disclose film forming agents useful in oral care compositions. The rapidly disintegrating films dissolve in the mouth and release functional components, typically flavorants.

It is known to incorporate flavorants, colorants, and some active components in films that dissolve in the oral cavity. These films are used either by themselves as breath freshening strips, teeth whitening strips, or as polymer flakes of monolayer films dispersed throughout an oral care composition.

Although some of these products have met with consumer approval, a flavor in most oral care products delivers only one signal to the consumers. Accordingly, there is still a need in the art for oral care products that can provide multiple signals to further improve performance and enhance product appeal.

SUMMARY

The present invention provides oral care products that employ a multilayer film technology in order to enhance, prolong or delay flavor delivery and provide extra flavor and other signals to consumers using these oral care products. As a result of using a multilayer film entrained in any orally acceptable carrier, oral care compositions are provided that have enhanced and prolonged flavor delivery, provide extra flavor signals, can deliver different and multiple flavor signals in delayed or controlled manner, change the flavor release profile, provide other signals resulting from incorporation of other ingredients and ensure customer compliance with good hygiene practices. Methods of their use are also provided.

In one embodiment, an oral care composition having enhanced flavor release comprising an orally acceptable carrier containing a first flavor and a multilayer film for extended or delayed flavor release is provided. The multilayer film includes at least a center layer containing a second flavor, the center layer positioned between two outer surface layers, each surface layer including a release modulating agent, the first and second flavor being the same or different. The multilayer film is retained on the oral surface after application and remains until eroded, thereby releasing additional flavor and other actives after application.

In another embodiment, the present invention provides an oral care composition comprising a multilayer film for extended release of flavor, the film entrained in an orally acceptable vehicle containing a first flavor, wherein the multilayer film includes a center layer containing a second flavor, the center layer being positioned between two outer surface layers, each outer surface layer including a film forming polymer, a release modulating agent and a mucoadhesive polymer. The multilayer film is retained on the oral surface after application and remains until eroded, thereby releasing additional flavor and other actives after application.

In yet another embodiment, an oral care composition is provided which includes an orally acceptable carrier containing a first flavor and a multilayer film for the delayed release of a flavor, the film including:

(a) a first outer surface layer;
(b) at least a first center layer containing a second flavor; and
(c) a second outer surface layer that can be the same or different from the first outer surface layer, the center layer positioned between the first outer surface layer and the second outer surface layer,
wherein the multilayer film is retained on the oral surface after application and remains until eroded, thereby releasing additional flavor and other actives after application.

The present invention also provides a method for enhancing flavor release from an oral care composition which comprises providing an oral care composition including an orally acceptable carrier containing a first flavor and a multilayer film for the extended release of a flavor, the multilayer film including at least a center layer containing a second flavor, the center layer positioned between two outer surface layers, the first and second flavor being the same or different, each outer surface layer including a release modulating agent and applying the oral care composition to an oral cavity of a mammal. The method further entails applying the oral care composition to the oral cavity whereby the composition is retained on an oral surface after application and erodes over time, thereby releasing additional flavor or active after application.

In another embodiment, the invention provides a method of preparing an oral care composition including a multilayer film for the delayed release of a flavor entrained in a orally acceptable carrier, which comprises:

(a) providing an orally acceptable carrier containing a first flavor;
(b) adding a multilayer film including at least a center layer containing a second flavor, the center layer positioned between two outer surface layers, the first and second flavor being the same or different, each outer surface layer including a release modulating agent; and
(c) homogenizing the mixture,
wherein the multilayer film is retained on the oral surface after application and remains until eroded, thereby releasing additional flavor and other actives after application.

BRIEF DESCRIPTION OF THE DRAWINGS

Preferred embodiments of the invention are described in the examples that follow, and illustrated in some of the figures appended hereto, in which:

In FIG. 3(a) the multilayer film does not contain Carbopol 971P. In FIG. 3(b) the multilayer film contains the mucoadhesive Carbopol 971P.

FIGS. 4(a) and 4(b) illustrate a three-layer film having the structure ABC, in which each layer is different. FIG. 4(a) illustrates the three-layer film embodiment, and FIG. 4(b) illustrates the release rate profile.

DETAILED DESCRIPTION

The present invention provides oral compositions and methods, for administration to, or use with a human or other animal subject. Preferably, specific materials and compositions to be used in this invention are, accordingly, pharmaceutically or cosmetically acceptable. As used herein, such a "pharmaceutically acceptable" or "cosmetically acceptable" component is one that is suitable for use with humans and/or animals to provide the desired therapeutic, sensory, decorative, or cosmetic benefit without undue adverse side effects (such as toxicity, astringent taste, irritation, and allergic response) commensurate with a reasonable benefit/risk ratio. The following definitions and non-limiting guidelines must be considered in reading and interpreting the description of this invention set forth herein.

The citation of references herein does not constitute an admission that those references are prior art or have any relevance to the patentability of the invention disclosed herein. All references cited in the Description section of this specification are hereby incorporated by reference in their entirety.

The description and specific examples, while indicating embodiments of the invention, are intended for purposes of illustration only and are not intended to limit the scope of the invention. Recitation of multiple embodiments having stated features is not intended to exclude other embodiments having additional features, or other embodiments incorporating different combinations of the stated features. Specific examples are provided for illustrative purposes of how to make, use and practice the compositions and methods of this invention and, unless explicitly stated to recite activities that have been done (i.e., using the past tense), are not intended to be a representation that given embodiments of this invention have, or have not, been performed. The description herein of certain advantages and disadvantages of known apparatus, methods, and compositions is not intended to limit the invention to their inclusion or exclusion. Indeed, certain embodiments of the invention include one or more known compositions, methods, or apparatus without suffering from the problems described herein.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

The oral care compositions of the various embodiments preferably are in the form of a dentifrice. The term "dentifrice" as used throughout this description, denotes a paste, gel, lozenge, gum, or liquid formulation. The dentifrice may be in any desired form, such as deep striped, surface striped, multilayered, having a gel surround the paste, or any combinations thereof. The film contained in the oral care composition may be of any desired shape or structure, including multiple small strips, or one continuous strip.

The expressions "carrier" or "aqueous carrier" as used throughout this description denote any safe and effective materials for use herein. Such materials include, for example, thickening agents, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

The present invention provides oral care compositions comprising a multilayer film entrained in an orally acceptable carrier, wherein the multilayer film includes at least a flavor containing center layer and at least one outer surface layer containing a film forming polymer and a release modulating agent for the delayed or prolonged release of the flavor from the multilayer film. As used herein, an "oral care composition" refers to a composition for which the intended use can include oral care, oral hygiene, or oral appearance, or for which the intended method of use can comprise administration to the oral cavity. Embodiments of the invention comprise a multilayer film.

As referred to herein, a "film" is a material having a substantially lamellar structure. A "lamellar" structure has, or is capable of having, a size in one or two dimensions (e.g., the x- or y-dimensions) that is substantially greater than the thickness of the structure in a third dimension (e.g., the z-direction). Lamellar structures among those useful herein include those that are substantially planar, layered, or lamelliform. In one embodiment, the lamellar structure is substantially planar, having a size in both the x- and y-dimensions that is substantially greater than the z-direction. In other embodiments, the lamellar structure is non-planar. In one embodiment, a film of this invention comprises a substantially continuous surface that can appear as a substantially flat surface, although in some embodiments the film may be deformed. In such embodiments, the film can have any of a number of shapes, including having a smooth curved surface. The fragments may be of a desired size and may be of regular or irregular perimeter.

Embodiments of this invention include multilayer films for delayed or extended release of a flavor from the center or core layer. It has been unexpectedly discovered that by utilizing multilayer films containing release modulating agents and mucoadhesives in the outer surface layers of the multilayer film, the flavor of an oral care composition can be released in an extended or delayed manner resulting in a burst of flavor that is more intense and longer lasting. Binding of the films to a surface in the oral cavity, which may include the gums, cheeks, tongue teeth and/or mucosa of the oral cavity allows the multilayer films to release their flavor over prolonged periods of time after brushing or rinsing with a mouthwash or oral rinse. That is, the films are retained on the oral surface even after brushing or rinsing with a mouthwash or oral rinse, and are eroded over time, thereby effecting sustained and prolonged release of flavor and other actives contained in the film. In addition, the presence of different layers in the film is believed to provide a larger surface area, thus ensuring delivery of high concentrations of flavor to the taste buds and olfactory center of the consumer.

As used herein the terms "extended," "sustained," "prolonged," or "delayed" release can be used interchangeably and describe the release of flavor and other actives from a delivery system such as a film over an extended period of time.

In one embodiment, the multilayer film contains at least a center layer containing a first flavor and two outer surface layers positioned around the center layer. Each film layer contains at least one film forming polymer, starch film forming agents, a sweetener, a humectant and a surfactant. The center layer further includes a flavor. In order to provide a delayed or prolonged release of the flavor from the center or core layer, the outer surface layers also include a release modulating agent. In some preferred embodiments, the outer surface layers may include more than one film forming polymer. In another embodiment, the multilayer films of the invention contain a plurality of centers layers, each capable of containing a flavor.

Non-limiting examples of film forming agents used to prepare the multilayer films of the present invention include an hydroxyalkyl cellulose such as hydroxypropyl methyl cellulose, hydroxypropyl cellulose, hydroxyethyl cellulose, hydroxyethylpropyl cellulose, hydroxybutyl methyl cellulose, hydroxy propyl methyl cellulose and carboxymethyl cellulose. Preferably the cellulose polymer is a low viscosity hydropropylmethyl cellulose polymer (HPMC). When HPMC is used as the film forming agent it is preferred that the HPMC have a viscosity in the range of about 1 to about 40 millipascal seconds (mPa·s) as determined as a 2% by weight aqueous solution of the HPMC at 20° C. using a Ubbelohde tube viscometer. Preferably the HPMC has a viscosity of about 3 to about 20 mPa·s at 20° C.

HPMC is available commercially from the Dow Chemical Company under the trade designation Methocel E5 LV. Methocel E5 LV is a USP grade, low viscosity HPMC having 29.1% methoxyl groups and 9% hydroxyproxyl group substitution. It is a white or off-white free-flowing dry powder. As a 2 wt. % solution in water as measured with a Ubbelohde tube viscometer it has a viscosity of 5.1 mPa·s at 20° C.

The outer surface layers can also include additional film forming agents such as other types of HPMC. In another embodiment, the outer surface layers include HPMC E50 such as Methocel™ E50 LV having a viscosity from 40 to 60 cps. These celluloses have higher viscosity than HPMC ES and as a result can be used to provide additional rate control for the sustained release of flavor from the center layer of the multilayer films of the present invention.

The hydroxyalkyl methyl cellulose is incorporated in the layers of the multilayer film in amounts ranging from about 25 to about 75% by weight and preferably about 40 to about 55% by weight of the multilayer film.

In other embodiments the outer surface layers of the multilayer film also include mucoadhesives. As used herein, the term "mucoadhesive" refers to hydrophilic polymers, natural or synthetic, which by the hydrophilic designation, can be either water soluble or swellable and which are adhesive to mucosal surfaces. Preferably such adhesives adhere the flavor released from center layers of the multilayer films to the mucosal tissues and/or teeth as well as functioning as a reservoir of this and other active substances which can be dissolved or absorbed via contacting the mucosal membrane.

Mucoadhesive polymers useful in the various embodiments described herein include, without limitation, carboxy polymethylene commercially available as Carbopol® CP940NF, CP971NF, CP974PNF, polyvinyl pyrrolidone ("PVP") commercially available as Plasdone K-90 USP, and polycarbophil available commercially as Noveon AA-1 USP (PC). Carbopol® and polycarbophil are commercially-available polymers from The Lubrizol Corporation, Wickliffe, Ohio, and generally consist of varying ratios of polyacrylic acid, cross-linked with polyalkenyl ethers or divinyl glycol. Other suitable materials for enhancing mucoadhesion include silica and zinc oxide.

Carbopol® 940 polymer is a cross-linked polyacrylate polymer known as a bioadhesive and also highly efficient rheology modifier capable of providing high viscosity to a composition. Polycarbophils are polymers of acrylic acid cross linked with divinyl glycol useful as bioadhesives and also in designing controlled-release formulations.

Preferably the mucoadhesive polymers are present in the film matrix of the present invention in an amount from 0.5% to 40%, more preferable in an amount from 1% to 20%, and most preferably in an amount from 2% to 10%.

Release modulating agents refer to agents that are utilized to extend or delay the delivery of flavor from the multilayer films of the present invention. Release modulating agents include polymers that are preferably water dispersible and swellable but frequently water insoluble or sparingly soluble. Non-limiting examples of release modulating polymers that extend or delay the release of flavor include polyvinyl acetate and hydroxyethyl cellulose. Release modulating agents also include zinc oxide and silica, especially when either or both of these materials are incorporated into the center flavor-containing layer(s).

As a result of the present invention, oral care formulations are provided including orally acceptable carriers and mucoadhesive, water erodible multilayer films that release flavor in an extended or prolonged manner and are removable from the oral cavity by the constant flow of saliva. As used herein, water erodible means a material or substance that does not dissolve in water or saliva in total, however will disintegrate and completely break apart upon exposure to water or saliva under the sheer conditions typically present in the mouth.

While multilayer films will be described with more particularity below, the release rate of the flavor from such films is determined by the rate at which these films dissolve or disperse in the fluid environment of the oral cavity, and by the diffusion rate at which the flavor is released from within the multilayer film. The release rate of the flavor from the multilayer film can be tailored to provide a range from minutes to hours as desired by adjusting the amount of the release modulating agent and/or the film forming agent in the multilayer film. For example, increasing the amount of polyvinyl acetate can reduce film swelling but increase the retention time of the film on the oral cavity mucosa and teeth thereby delaying the release of the flavor from the core layers of the multilayer films of the invention.

In one preferred embodiment, the release modulating agent present in the films of this invention varies from 0.1% to 30% and more preferably from 0.5% to 20% and most preferably from 5% to 20%. Further, the amount of polymeric base preferably varies from 5% to 80% more preferably from 25% to 75% and most preferably from 40% to 50%.

Adjusting the content of the flavor present in the center layer of the multilayer films of the invention also can be used to control, extend or delay the release of the odor controlling active. Preferably, the amount of the flavor present in the multilayer films of the invention varies from 1% to 40% and more preferably from 2% to 30%, and most preferably from 5% to 25%.

Cold water swellable, physically modified and pregelatenized starches are particularly useful as texture modifier to increase the stiffness of the hydroxyalkyl methyl cellulose multilayer films of the present invention. In the preparation of such starch products, the granular starch is cooked in the presence of water and possibly an organic solvent at a temperature not higher than 10° C. higher than the gelatinization temperature. The obtained starch then is dried.

Pregelatinized corn starch is available commercially. A preferred starch is available under the trade designation Cerestar Polar Tex-Instant 12640 from the Cerestar Company. This Cerestar starch is a pregelanterized, stabilized and crosslinked waxy maize starch. It is readily dispersible and swellable in cold water. In its dry form, it is a white free flowing powder with an average flake size no greater than 180 micrometers and 85% of the flakes are smaller than 75 micrometers. It has a bulk density of 44 lbs/ft.$^3$ The Cerestar starch has excellent cold storage and freeze-thaw stability. It has a rapid hydration rate and can reach extremely high viscosity without cooking. It has a smooth and creamy texture similar to cook-up starches. It also has excellent paste clarity and a bland flavor.

The pregelatinized starch is present in the film matrix of the present invention in an amount ranging from about 0 to about 50% by weight and preferably about 10 to about 20% by weight.

Sweeteners also may be incorporated in the layers of the multilayer films of the present invention include both natural and artificial sweeteners. Suitable sweeteners include water soluble sweetening agents such as monosaccharides, disaccharides and plysaccharides such as xylose, ribose, glucose (dextrose), mannose, glatose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame). D sucralase sweetener is preferred in one aspect of this invention.

In general, an effective amount of sweetener is utilized to provide the level of sweetness desired for a particular film matrix composition, will vary with the sweetener selected. This amount will normally be 0.01% to 2% by weight of the composition. However, in some embodiments additional sweetener may be added to the toothpaste directly to ensure the continuous perception of sweetness specifically during the initial use period.

In certain embodiments, it may be desirable to increase the wettability of the multilayer film by adding surfactants. Any orally acceptable surfactant, most of which are anionic, non-ionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxylate, sulfate, sulfonate, phosphate or phosphonate. A suitable example is cocoamidopropyl betaine.

Edible non-ionic surfactants are preferred. Examples of edible non-ionic surfactants that may be used include polyoxyethylene sorbitan fatty acid esters, polyoxyethylene alkyl ethers, and polyoxyethylene caster oil derivatives. An example of a suitable commercially available non-ionic surfactant that may be used is polysorbate 80, which is a mixture of oleate esters of sorbitol and sorbitol anhydrides, consisting predominantly of the monoester, condensed with approximately 20 moles of ethylene oxide. Polysorbate 80 is sold as Tween® 80 by ICI Surfactants is most preferred for the multilayer films of the present invention. HLB value of the polyoxyethylene sorbitan fatty acid ester should be greater than 10, but should not exceed 20. The inclusion of a surfactant has proven very beneficial in many cases. One or more surfactants optionally are present in a total amount of 0.01% to 10%, for example 0.05% to 5% or 0.1% to 2% by weight of the composition.

The center or core layer of the multilayer films of the present invention preferably includes at least one flavor agent. Flavor agents incorporated in the multilayer films of the present invention are known to the prior art, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. Generally, any flavoring or food additive, such as those described in Chemicals Used in Food Processing, publication 1274 by the National Academy of Sciences, pages 63-258, may be used. Generally the flavoring agent is incorporated in the film of the present invention in an amount ranging from about 1 to about 60% by weight, preferably from about 5% to about 40%, more preferably from about 15% to about 25% by weight.

The release profile of flavor during brushing or rinsing can be controlled by balancing the thickness and/or composition of the outer surface layers. The thickness of the outer surface layers can vary from 0.2 mils to 4 mils.

Without being bound by theory, it is believed that upon contact with saliva or water, the multilayer film flavored chips of the present embodiments begin to slowly disintegrate since each layer and especially the outer surface layers are water erodible. Moreover, when exposed to water or saliva, the mucoadhesivity of the outer layers of the multilayer film becomes activated, which leads to the rapid sticking to soft and/or hard tissue in the mouth. Once the films adhere to the oral surfaces, they provide an effective reservoir for further release of flavor and actives. The multi-layer films continue to slowly disintegrate over time, sequentially releasing the contents of each layer once the layer immediately exterior to it disintegrates. As a result of incorporating multilayer film flavored chips in a dentifrice or a mouth rinse, the consumer can use oral care compositions that have enhanced flavor delivery. As the flavor of the toothpaste or mouth rinse wanes, the flavor released from the multilayer film flavored chips increases as the flavor from the core layer of the multilayer film chips is released and the consumer experiences an increased flavor sensation long after the flavor from a conventional dentifrice has diminished.

In one embodiment, the flavor of the toothpaste is enhanced by adding to it the multilayer film flavored chips of the present invention, wherein the flavor of the chips is the same as that of the toothpaste.

Extra flavor signals can be delivered by varying the kind of flavor contained in the multilayer films of the present invention. When the flavor of the toothpaste and the one contained in the multilayer film is the same, the intensity of the flavor during brushing increases.

In another embodiment, the perception of flavor can be changed over time by incorporating in the orally acceptable carrier multilayer films having the structures AB, ABA or ABC. Other multilayer film structures are also available such as ABAB or ABCABC. In these film structures, A represents an outer surface layer that preferably includes a film forming polymer selected from the group consisting of hydroxypropylmethyl cellulose, methyl cellulose, hydroxypropyl cellulose and mixtures of copolymers thereof. The outer surface layer A will preferably include corn starch, a sweetener such as D sucralase, a humectant such as propylene glycol and a surfactant such as Tween 80. The surface layer A can include other ingredients that can delay or speed up the flavor release from the center layer. Such ingredients include but are not limited to release modulating polymers such as polyvinyl acetate or hydroxyethyl cellulose. The thickness of the outer surface layers can vary and thus also impact the flavor release from the center layer. When the outer surface layers are thin or about 0.2 mil the flavor release from the center layer is accelerated. Conversely when the outer surface layer have increased thickness, the flavor released from the center layer is delayed. Preferably the thickness of the outer surface layers is about 0.55 mils. The center or core layer B can include the same components as the outer surface layer A, however, layer B also contains a flavor that can be the same or different from the flavor of the orally acceptable carrier. The center layer B can also include other ingredients that can provide additional sensation signals to complement the enhanced flavor signal. When the structure is ABA, the flavor release occurs at different time points following a pattern as discussed with respect to FIG. 1 below. When the multilayer film structure is ABC, the flavor perception also changes over time, as discussed with respect to FIGS. 4(a) and 4(b) below.

In one embodiment varying the composition of the outer surface layers can be used to control the release time of a second flavor signal from the toothpaste or mouth rinse that incorporates the multilayer film flavored chips of the present invention. For example, the flavor release from the center layer can be delayed by adding to the outer surface layers a release modulating polymer such as polyvinyl acetate, hydroxylethyl cellulose and the like in an amount effective to delay the release of the flavor from the center layer for the desired amount of time. For example, by adding from about 5 wt % to about 30 wt % of polyvinyl acetate, the flavor release may be delayed by 5 to 30 minutes after brushing thereby providing an extended or sequential burst of flavor release.

In another embodiment, varying the thickness of the outer surface layers can be used to control the time of a second flavor signal from the toothpaste that incorporates the multilayer film flavored chips. For example, the thickness of the outer surface layers can vary from 0.2 mil to 4 mil.

In yet another embodiment, the present invention provides a toothpaste that can supply a second flavor signal having an intensity that is different from the intensity of the first flavor signal of the multilayer flavored chips. This can be accomplished by varying the concentration of the flavor in the slurry composition utilized for the center or core film layer of the multilayer flavored chips. For example, the flavor level in the center or core flavor bearing layer can vary from 5% to 40% by weight of the center or core layer composition.

In various embodiments, by preparing the multilayer flavored chips with a flavor that is different from that of the toothpaste base, a toothpaste can be obtained that can deliver a second flavor signal that is different from a first signal. In various other embodiments, multilayer film chips can be prepared to deliver other signals in addition to flavor signals in which the flavor of the core layer is supplemented with one or more agents selected from the groups consisting of a cooling sensation signal, a tingling sensation signal, a sweet sensation signal, a warming signal or a mixture thereof.

Examples of cooling sensation agents that provide a cooling sensation signal include without limitation menthol, WS-3™, WS-5™, WS-23™ and L-menthyl lactate. Examples of tingling sensation agents that provide a tingling sensation signal include without limitation spilanthol and capsiacin. Examples of sweet sensation agents that provide a sweet sensation include without limitation saccharin, sucralose, aspartame, neotame, and acesulfame-K. Examples of warming sensation agents that provide a warming sensation include without limitation cinnamic aldehyde, capsaicin, zeolites, and capsicum oleoresin.

The multilayer film thickness ranges in size from 1.0 mils to 10 mils and preferably 1.5 mils to 4 mils. The dried film of the present invention then may be cut or punched into shaped flakes having a particle size of 0.01 to 0.50 inches preferably 0.08 to 0.25 inches.

Additional stability can be provided to the shapes formed from the dried multilayer film, by applying to the film, before shaping into flakes or chips, a protective barrier overcoat such as a food grade shellac or ethyl cellulose.

When the film is to be used for decorative effect, the film once formed is punched into various attractive shaped flakes such as hearts, stars, diamonds and circles. The film flakes are incorporated in the base dentifrice of the present invention at a concentration of 0.05 to 2.0% by weight and preferably 0.2 to 0.75% by weight.

Methods of Preparing Films

The multilayer films of the present invention can be prepared using methods known in the art such as conventional extrusion, aqueous and solvent casting processes. In one embodiment a three layer film is provided. The three layer film can be formed by successively forming the layers A, B, A by casting from a respective slurry and subsequent drying for each layer. For example, the first layer can be cast from a slurry composition including film-forming polymer as a 5 mils layer, and then dried for 15 minutes in an oven at a temperature of 95° C. Then, the second layer can be cast over the first layer from a slurry composition including a film-forming polymer and a flavor as a 15 mils layer, and then dried for 15° C., minutes in the oven at 95° C. Finally, the third layer can be cast over the second layer from a slurry composition including a film-forming polymer as a 5 mils layer, and then dried for 15 minutes in an oven at a temperature of 95° C. Other means to produce 2-layer, 3-layer and multilayer films are well known to the art and include aqueous casting, solvent casting, extrusion, and the like. Films can be made sequentially, such as illustrated above, or formed as a multilayer laminar slurry directly from the component slurries. The laminar slurry would then be dried in a similar manner. Combinations of methods are also possible. For example, extrusion of layers can be followed by solvent casting of different layers. It is not the intent of this description to limit the manner in which the film is crafted. After the multilayer films are prepared, they can be cut into smaller fragments of different shapes or forms, such as chips for inclusion into a toothpaste or mouthwash base.

In another embodiment, the present invention provides a three-layer film wherein the outer surface layers are water erodible and include a film forming polymer, while the center layer incorporates a flavor and a second film forming polymer which may be the same or different from the film forming polymer of the center layer.

In yet another aspect, the invention provides a method for enhancing flavor release from an oral care composition which includes providing an oral care composition including an orally acceptable carrier containing a first flavor and a multilayer film for delayed flavor release, the multilayer film including at least a center layer containing a second flavor, the center layer disposed between two outer surface layers, the first and second flavor being the same or different, each outer surface layer including a release modulating agent and applying the oral care composition to an oral cavity of a mammal.

The first flavor contained in the toothpaste or mouthwash carrier is released from 0 minutes to 5 minutes as measured by flavor levels present in saliva from the beginning of use of the oral care composition. The second flavor contained in the multilayer film is released from 0 minutes to 45 minutes, or from 10 minutes to 20 minutes, as measured by flavor levels present in saliva from the beginning of use of the oral care composition. As referred to herein "peak flavor" refers to the maximum release of flavor from the oral care composition of the invention and it occurs after the first flavor of the carrier decreases to about 0.5 of its highest value and the second flavor released form the multilayer film reaches it highest value as measured by flavor level present in saliva of the mammal. The peak flavor of the oral care composition of the present invention can reach a maximum flavor intensity from 2 minutes to 60 minutes, preferably from 5 minutes to 30 minutes, and most preferably from 5 minutes to 20 minutes after the use of the oral care composition is complete. In one preferred embodiment, a peak flavor is reached within from 10 minutes to 15 minutes after the first flavor of the toothpaste or mouthwash base is consumed in its entirety.

Figure 1:
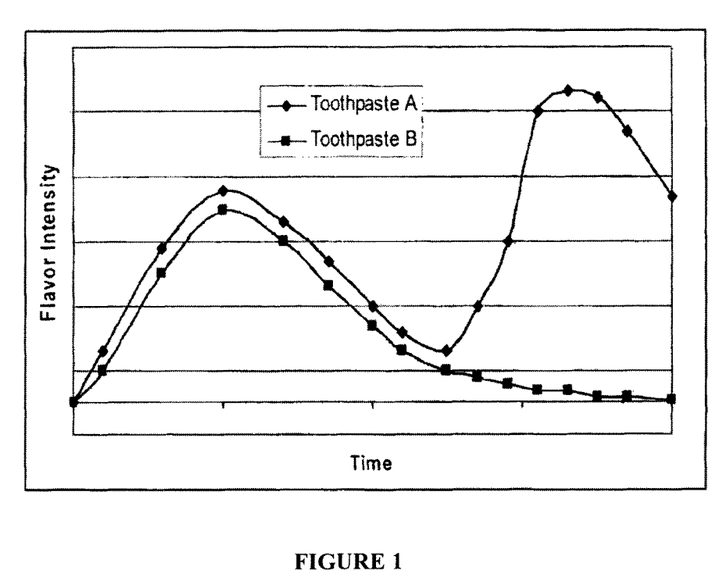
FIG. 1 illustrates the flavor release profile of toothpaste A containing multilayer flavored chips of the present invention and the flavor release profile by conventional toothpaste B.
Figure 2:
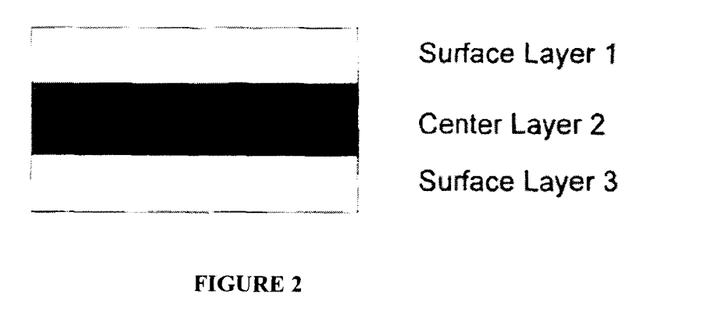
FIG. 2 illustrates a three layer film where in the center or core layer contains a flavor and the two outer surface layers are without a flavor.

The overall benefits provided by the multilayer films of the present invention also are illustrated in FIG. 1. FIG. 1 illustrates typical release profiles of toothpaste A and toothpaste B measured by flavor levels in saliva taken during brushing time. Toothpaste A contains its own flavor but also 3-layer film flavored chips prepared from a 3-layer film having the structure ABA as shown in FIG. 2 wherein the outer surface layers A have the same composition and the core layer B is the only layer containing a flavor. Toothpaste B does not contain any flavor chips and has the flavor content of conventional toothpaste. As shown in FIG. 1, initially the flavor release profile of toothpaste A follows the release profile of a conventional toothpaste B. However, after the flavor of the toothpaste base is consumed, as the 3-layer flavored chips start to melt, the flavor from the center layer is released and the consumer experiences a sudden and intense burst of flavor. As described in more detail below, the intensity of the burst of flavor varies with the amount of flavor in the center layer of the multilayer film chips of the present invention.

Figure 3A:
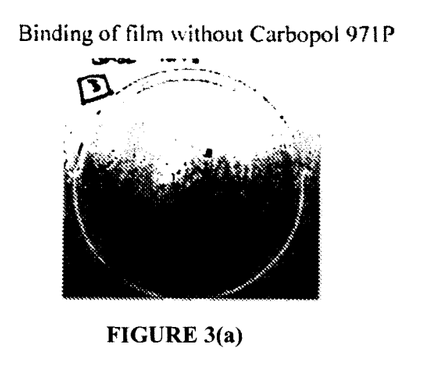
FIGS. 3(a) and (b) illustrate the effect of Carbopol 971P on the binding of a multilayer film of ABA configuration onto an artificial skin surface.
Figure 3B:
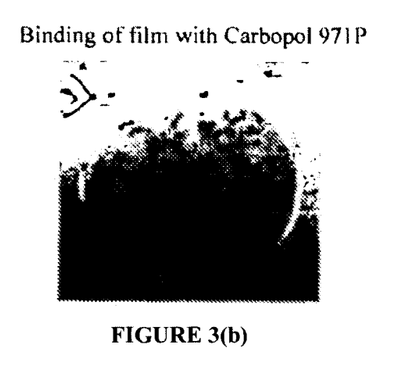

FIG. 2 illustrates a 3-layer film having the structure ABA wherein the outer surface layers have the same compositions. FIGS. 3(a) and (b) illustrate the effect of Carbopol 971P on the binding of a multilayer film of ABA configuration onto a model for the saliva-coated oral mucosa. In FIG. 3(a) the multilayer film does not contain Carbopol 971P. In FIG. 3(b) the multilayer film contains the mucoadhesive Carbopol 971P. It can be seen from FIG. 3(b) that the multilayer film containing a mucoadhesive shows increased adherence to the saliva-coated surface.

Figure 4A:
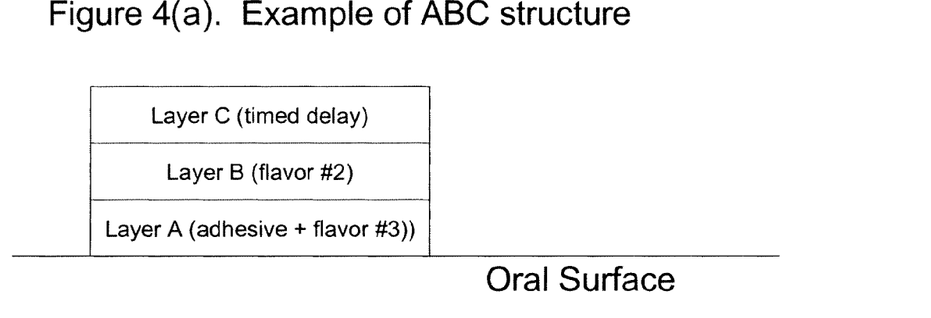
Figure 4B:
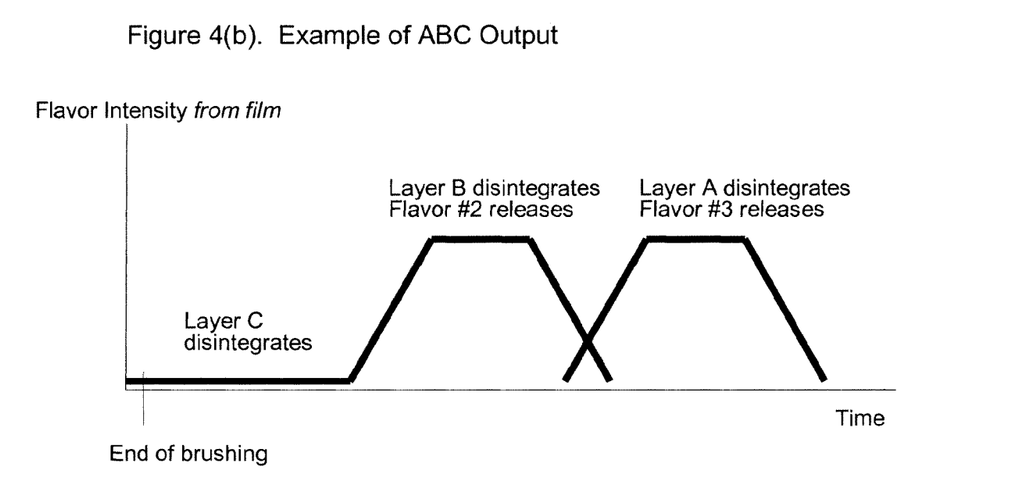

FIG. 4(a) illustrates a 3-layer film having the structure ABC wherein the surface layer A adjacent the oral surface includes an adhesive and flavor #3, the middle layer B contains flavor #2, and the surface layer C positioned away from the oral surface is a timed delay layer. FIG. 4(b) illustrates the release profile of the various flavors realized after brushing. The adhesive material used in surface layer A provides the film with the ability to adhere to an oral surface. Over a period of time after brushing, surface layer C disintegrates, and then the flavor #2 is released from middle layer B. Once middle layer B disintegrates and releases flavor #2, surface layer A begins to disintegrate and release flavor #3. Flavor #2 and flavor #3 could be replaced with a cooling agent, both could be different cooling agents, both could be the same flavor in differing concentrations, as will be appreciated by those having ordinary skill in the art.

In various embodiments, the oral care compositions comprise a plurality of lamellar multilayer film fragments entrained in a carrier. In one embodiment, the composition comprises a multilayer film, wherein the film comprises lamellar fragments of the film material. In one embodiment, the composition comprises a carrier having distributed therein a plurality of lamellar fragments, wherein the fragments comprise a multilayer film wherein the core layer contains a flavor. Such fragments may be of any of a variety of shapes or forms, including semi-solid or solid discrete portions, fragments, particles, flakes, or combinations thereof. In various embodiments, the multilayer film comprises a first plurality of fragments and a second plurality of fragments, wherein the first plurality of fragments differ in composition or appearance from the second plurality of fragments. Such difference in composition or appearance can be in any aspect of the composition of the fragment (e.g., different film components, different functional material, different formulation colorant), different appearance (e.g., shape, color, texture, refractive index, reflective index), or combinations thereof.

In various embodiments, the fragments exhibit perceivable contrast with the carrier. The perceivable contrast can be sensory contrast, such as optical contrast, tactile contrast, taste contrast, or olfactory contrast. In some configurations, optical contrast can be color contrast, or a difference in refractive index or reflective index. In some configurations, color contrast can be imparted by one or more colorants that comprise different components of the composition. In various embodiments, the present invention provides compositions comprising a plurality of film fragments in a carrier, wherein said fragments are visibly discernable. As referred to herein, "visibly discernable" refers to one or more characteristics of a fragment which cause the fragment to have a different physical appearance, preferably to the naked eye, relative to the carrier in which the fragment is entrained. Such characteristics include color, opacity, refractive index, reflective index, size, shape, and combinations thereof.

In various embodiments, the fragments have a non-random shape. In one embodiment, a "non-random" shape is a shape which results from a manufacturing process of shaping, cutting, or other forming process by which a specific shape is imparted to a fragment. In such embodiments, a non-random shape is distinguished from such shapes that result from simple precipitation or grinding of a material. In one embodiment, a "non-random" shape is "repeating," wherein the composition comprises a plurality of fragments have substantially the same shape. Such repeating shape may have any of a variety of forms, and may be selected based on a variety of aesthetic or functional criteria. In certain embodiments, the shape of a film fragment can be a recognizable shape. In certain embodiments, a multilayer film fragment can comprise a nonrandom shape. Such shapes include simple geometric shapes, such as polygons and elliptical shapes, such as triangles, quadrilaterals (such as a square, a rectangle, a rhombus), pentagons, hexagons, oval, and circles. In one embodiment, the repeating shape is a square. Repeating shapes include, in other embodiments, shapes that are representative of figures or animate or inanimate objects, such as stars, hearts, gems, flowers, trees, shamrocks, a letter of an alphabet, numbers, animals, people, and faces. In various embodiments, the composition comprises a single repeating shape. In other embodiments, the composition comprises a plurality of fragments having a plurality of repeating shapes. In one embodiment, the compositions of the present invention comprise a plurality of first multilayer film fragments having a first repeated shape and a plurality of second multilayer film fragments having a second repeated shape, wherein the first repeated shape is different from the second repeated shape.

In various embodiments, the size of the fragments is not critical, and may be determined pursuant to any of a variety of criteria, including manufacturing convenience, affect on visual appearance, surface area, affect on texture in the composition, and combinations thereof. In some embodiments, the multilayer film fragments can be up to about 1 inch (25.4 mm) in length in the longest dimension. As referred to herein, "long dimension" is the dimension of a fragment in length or width (i.e., in the x- and y-dimensions, as the fragment is, or is deformed to be, in a planar shape) in a dimension substantially perpendicular to the "thickness" or shortest dimension of the fragment (i.e., the z-dimension). It is understood that in various embodiments comprising a plurality of fragments, the fragments may be present in a range of sizes due to a variety of factors, including random variation in size, manufacturing tolerances, and intentional sizing or mixing of the fragments through sieving or similar means. As referred to herein, sizes refer to the average size of fragments in a given plurality of fragments.

In various embodiments, the fragments are from 0.2 mm to 15 mm in long dimension. In various embodiments, the long dimension of the fragments is from 0.2 mm to about 10 mm, from 0.5 mm to 10 mm, from 0.8 mm to 8 mm, from 0.9 mm to 5 mm, from 1.0 mm to 5 mm, or from 1.5 mm to 2.5 mm. In some embodiments, the long dimension of the fragments is at least 3 min, and can be from 6 mm to 13 mm. In certain embodiments, a plurality of film fragments are greater than 600 microns in the longest dimension. In certain embodiments, a plurality of film fragments are greater than about 1 millimeter in the longest dimension.

In various embodiments, the fragments of the present invention have a thickness of from about 1 mil (thousandth of an inch, 25.4 microns) to 3 mils (76.2 microns). In various embodiments, the fragments have a thickness of less than 4 mils or less than 100 microns and from 0.1 mils (2.54 microns) up to about 10 mils (254 microns), from 0.5 mils (12.7 microns) up to 5 mils (127 microns), from 1.4 mils (35.6 microns) to about 2.0 mils (50.8 microns).

In some embodiments, the compositions of the present invention comprise fragments having an aspect ratio of at least about 5:1. As referred to herein, "aspect ratio" of a fragment is the ratio of the diameter of the smallest imaginary sphere that can enclose the object to the diameter of the largest imaginary sphere that can be completely inside the object and tangent to the surfaces of the object. For example, the aspect ratio of a sphere is 1:1; in another example, the aspect ratio of a cylinder that is 2 inches (50.8 mm) long and ¼ inch (6.35 mm) in diameter is slightly over 8:1; in yet another example, a multilayer film fragment of the present invention that is 1 mil (25.4 microns) in thickness, 1 inch (25.4 mm) in length, and 1 inch (25.4 mm) wide has an aspect ratio of about 1414:1.

In some embodiments, the compositions of the present invention comprise fragments having an aspect ratio of at least 10:1. In various embodiments, the fragments have an aspect ratio of from 5:1 to 10,000:1, from 5:1 to 500:1, from 10:1 to 1,000:1, from 10:1 to 100:1, from 20:1 to 100:1, or from 25:1 to 35:1.

In various embodiments, the multilayer film comprises a formulation colorant that imparts a color to the multilayer film, the composition, or both. In various embodiments, the film fragments contrast with the carrier, and are white, black, or of any color that is visible against or contrasts with the carrier background. Formulation colorants among those useful herein include non-toxic water soluble dyes or pigment, such as, for example, metallic oxide "lakes." In certain embodiments, the colorant is approved for incorporation into a food or drug by a regulatory agency, such as FD&C or D&C pigments and dyes approved by the FDA for use in the United States. Colorants among those useful herein include FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-Δ-3,5-cyclohexadienimine], FD&C Blue No. 1 (disodium salt of dibenzyldiethyl-diaminotriphenylcarbinol trisulfonic acid anhydrite), FD&C Blue No. 2 (sodium salt of disulfonic acid of indigotin), and mixtures thereof in various proportions. In one embodiment, the colorant comprises a water insoluble inorganic pigment, such as titanium dioxide, chromium oxide green, phthalocyanine green, ultramarine blue, ferric oxide, or a water insoluble dye lake. In some embodiments, dye lakes include calcium or aluminum salts of an FD&C dye such as FD&C Green #1 lake, FD&C Blue #2 lake, D&C Red #30 lake or FD&C #Yellow 15 lake. In certain embodiments, a water soluble dye, such as, for example, FD&C Blue #1, is contained within a water-insoluble polymer such as, for example polyethylene such as that found in polyethylene beads (e.g., Microblue Spectrabeads, sold by Micropowders, Inc.). In certain embodiments, the multilayer film comprises a dye such as D&C Red #30. In certain embodiments, a white colorant is used, for example titanium dioxide ($TiO_2$), titanium dioxide coated mica (e.g., Timiron), a mineral, or a clay. In certain embodiments, the colorant is a non-bleeding dye. In various embodiments, the multilayer film comprises a colorant at a level of from about from 0.5% to 20% by weight of the multilayer film, or from 1% to 15% by weight of the multilayer film, or from 3% to 12% by weight of the film. In one embodiment, the compositions of the present invention comprise a first plurality of multilayer film fragments comprising a first color, and a second plurality of multilayer film fragments comprising a second color. Preferably, the second color is different than the first color.

The multilayer film of the present invention, in various embodiments, disintegrates during use of the composition. In other embodiments, the multilayer film does not disintegrate during use of the composition. In some embodiments, the multilayer film releases a material, such as the flavor, into the carrier. As referred to herein, "disintegrate" refers to physical disruption of the multilayer film or fragment material, so as to produce a film or film fragments of reduced size compared to the original film. Such disruption may be through mechanical, chemical, or physical-chemical means. The disintegration can result, for example, from shearing, grinding, or exposure to elevated temperatures during use. In various dentifrice embodiments of the present invention, such disintegration results from brushing of the composition on the teeth of the subject using the composition. In one embodiment, the film disintegrates so as to release a functional flavor material (as further described herein). In some embodiments, a film fragment can disintegrate into small pieces that are not visually discernable. In some embodiments, the film fragments disintegrate to collectively form a colloid or gel.

In various embodiments, the multilayered films of the present invention may include, in addition to the flavorant and without limitation, other functional actives such as:
  A. masking fragrances such as ionones,
  B. bacteriostatic or antibacterial agents such as magnolia bark extract, magnolol, honokiol, triclosan, cetyl pyridinium chloride (CPC), chlorhexidine, and the like,
  C. metal salts of bismuth, zinc, stannous, copper and the like.

In various other embodiments, the multilayer film may comprise, without limitation, and in addition to the flavorant other therapeutic actives. As referred to herein, a therapeutic active is a material that is useful for the prevention or treatment of a physiological disorder or condition. Such disorders or conditions include those of the oral cavity (including the teeth and gingiva), skin, hair, and eyes. The specific therapeutic active is preferably determined according to the desired utility of the composition. In one embodiment, the release of flavor provides a valuable signal to the user that the therapeutic active has enough time to work effectively in the mouth. Such actives include the following:
  A. antimicrobial agents, such as triclosan, cetyl pyridium chloride, domiphen bromide, quaternary ammonium salts, sanguinarine, fluorides, alexidine, octonidine, EDTA, essential oils such as thymol, methyl salicylate, eucalyptol and menthol, and the like,
  B. non-steroidal anti-inflammatory drugs, such as aspirin, acetaminophen, ibuprofen, ketoprofen, diflunisal, fenoprofen calcium, naproxen, tolmetin sodium, indomethacin, and the like,
  C. anti-tussives, such as benzonatate, caramiphen edisylate, menthol, dextromethorphan hydrobromide, chlophedianol hydrochloride, and the like,
  D. decongestants, such as pseudoephedrine hydrochloride, phenylepherine, phenylpropanolamine, pseudoephedrine sulfate, and the like,
  E. anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like,
  F. expectorants, such as guaifenesin, ipecac, potassium iodide, terpin hydrate, and the like,
  G. anti-diarrheals, such a loperamide, and the like,
  H. $H_2$-antagonists, such as famotidine, ranitidine, and the like; and
  I. proton pump inhibitors, such as omeprazole, lansoprazole, and the like,
  J. general nonselective CNS depressants, such as aliphatic alcohols, barbiturates and the like,
  K. general nonselective CNS stimulants such as caffeine, nicotine, strychnine, picrotoxin, pentylenetetrazol and the like,
  L. drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like,
  M. antiparkinsonism drugs such as levodopa, amantadine and the like,
  N. narcotic-analgesics such as morphine, heroin, hydromorphone, metopon, oxymorphone, levorphanol, codeine, hydrocodone, xycodone, nalorphine, naloxone, naltrexone and the like, O. analgesic-antipyretics such as salycilates, phenylbutazone, indomethacin, phenacetin and the like, P. psychopharmacological drugs such as chlorpromazine, methotrimeprazine, haloperidol, clozapine, reserpine, imipramine, tranylcypromine, phenelzine, lithium and the like.

The amount of medicament that can be used in the films of the present invention can be dependent upon the dose needed to provide an effective amount of the medicament.

In various embodiments, therapeutic agents useful herein include anticaries agents, tartar control agents, antiplaque agents, periodontal actives, breath freshening agents, malodour control agents, whitening agents, antibacterials, steroids, anti-inflammatory agents, vitamins, proteins, conditioning agents, moisturizers, antiperspirant actives, deodorant actives, anesthetics, and mixtures thereof.

In certain oral care embodiments, the multilayer film or the oral care composition may comprise an oral care active, which is useful for the prevention or treatment of an oral care disorder or condition. Oral care actives among those useful herein include abrasives, anticaries agents, tartar control agents, antiplaque agents, periodontal actives, breath freshening agents, malodour control agents, tooth desensitizers, salivary stimulants, whitening agents, and combinations thereof. Active materials among those useful herein are described in U.S. Pat. No. 6,596,298 to Leung et al.

Tartar control agents among those useful herein include dialkali or tetraalkali metal pyrophosphate salts such as $Na_4P_2O_7$, $K_4P_2O_7$, $Na_2K_2P_2O_7$, $Na_4H_2P_2O_7$ and $K_2H_2P_2O_7$; long chain polyphosphates such as sodium hexametaphosphate; and cyclic phosphates such as sodium trimetaphosphate. In some configurations, a polyphosphate is a β-phase calcium pyrophosphate, such as disclosed in U.S. Pat. No. 6,241,974 to White, Jr. In some embodiments, the film comprises an anticalculus agent at a level of about 15 to 20% by weight of the film.

Odor reducing agents useful herein include sulfur precipitating agents. Such sulfur-precipitating agents include metal salts, such as a copper salt or a zinc salt. Such salts include copper gluconate, zinc citrate and zinc gluconate. These zinc salts can be used in combination or in addition to the zinc compounds included in the film. In various embodiments, the film comprises sulfur precipitating agents at a level of from 0.01 to 30% by weight of film, from 2% to 2.5% by weight of film, or 10% to 20% by weight of film.

In a certain embodiments, the film and/or oral composition may include a saliva stimulating agent (a "succulent"). Such agents include those disclosed in U.S. Pat. No. 4,820,506 to Kleinberg et al. In some configurations, a saliva stimulating agent can include a food acid such as citric, lactic, malic, succinic, ascorbic, adipic, fumaric and tartaric acids. In various embodiments, the film comprises a saliva stimulating agent at a level of from 0.01 to 12% by weight of the film, from 1% to 10% by weight of the film, or from 2.5% to 6% by weight of the film. In some embodiments, a saliva stimulating agent can be used in the amelioration of dry mouth.

In certain oral care embodiments, the multilayer film comprises other active materials, such as antibacterial agents such as magnolia extract, triclosan, grapeseed extract, thymol, methyl salicylate, eucalyptol, menthol, hop acids, cetyl pyridinium chloride, (including CPC/Zn and CPC+enzymes) and usnic acid; anti-inflammatory agents such a breath freshening agents (for example zinc gluconate, zinc citrate, zinc chlorite and alpha ionone); tooth desensitizers such as potassium nitrate, desensitizing polymers, and desensitizing minerals; anti-inflammatory agents such as magnolia extract, ursolic acid; aloe, and cranberry extract; vitamins such as pantheon, retinyl palmitate, folic acid, tocopherol acetate and Vitamin A; herbs or herbal extracts such as rosemary, oregano, chamomilla recutita, *mentha piperita, salvia officinalis*, orcommiphora and myrrha; proteins, such as milk proteins and enzymes such as peroxide-producing enzymes, amylase, plaque-disrupting agents such as papain, glucoamylase, glucose oxidase, and "next generation" enzymes; whitening agents such as hydrogen peroxide, urea peroxide and phosphate salts; medicinals, such as aspirin (acetyl salicylic acid), caffeine, and benzocaine; probiotics; abrasives such as silicas (including high cleaning silica); anti-caries agents such as stannous salts (e.g., stannous fluoride) or amino fluoride; a nitric oxide synthase inhibitor such as guanidinoethyldisulfide; calcium; anti-attachment ingredients, such as polyvinylphosphonic acid; preservatives such as Solbrol® (Bayer Chemicals AG); silicones; chlorophyll compounds, anti-leukoplakia agents such as beta-carotene; anti-oxidants such as Vitamin E; and combinations thereof. In some embodiments, the films comprise such active materials at a concentration of 0.01 to 30% by weight of film, from 2% to 25% by weight of the film, or from 10% to 20% by weight of film.

In certain embodiments, the multilayer film and/or oral care composition includes a preservative. A preservative can be added in amounts from 0.001 wt % to 5 wt %, preferably from 0.01 wt % to 1 wt % of the multilayer film. Non-limiting examples of preservatives include sodium benzoate and potassium sorbate.

The compositions of the present invention comprise a carrier in which a multilayer film, or fragments, is entrained. As referred to herein, a "carrier" is any material or composition in which a multilayer film can be entrained and is suitable for administration or application to the human or animal subject to whom the composition is administered or applied. As referred to herein, "entrained" refers to the embedding or suspension of a multilayer film in a carrier. In various embodiments comprising a plurality of fragments, such fragments may be entrained by embedding, suspension, dispersion or other distribution of the fragments in the carrier. In various embodiments, the fragments are distributed substantially homogenously throughout the carrier. In other embodiments, the fragments are not distributed homogenously in the carrier. In certain embodiments, the distribution of a plurality of multilayer film fragments is substantially isotropic within the carrier. Dentifrice compositions that include a plurality of film fragments dispersed or suspended in a carrier are commercially available under the tradename Max Fresh® or Max White®, from Colgate-Palmolive Company, New York, N.Y.

The compositions of the embodiments may be described as comprising two phases, wherein one phase comprises a carrier and a second phase comprises the aforementioned film or fragment. The term "phase" as used herein denotes a physical phase as understood in the physical and material sciences, i.e., a portion of a material whose properties and composition are uniform. However, a phase as used herein can be discontinuous, i.e., a phase can comprise a plurality of separate components. For example, a plurality of polymer film fragments of identical composition is considered to comprise a single phase. In some embodiments, a multilayer film fragment can be entirely embedded within the material comprising the first phase, or totally or partially exposed on the surface of the first phase. For example, if the composition is a dentifrice comprising both a gel and multilayer film fragments, a film fragment can be totally surrounded by the gel, or partially or totally exposed on the surface of the gel. In certain embodiments, compositions comprise more than two phases. Such multi-phase compositions include those having two carriers, each of which contributes a phase to the composition, in addition to film fragments as described herein. Other multi-phase compositions include those having a single carrier and two or more pluralities of fragments, wherein the pluralities of fragments have differing compositions.

In various embodiments, the carrier is a liquid, semi-solid or solid. A "liquid" can be a liquid of low or high viscosity. A liquid can be a liquid such that flow is imperceptible under ambient conditions. For example, a soap, such as an ordinary bar of hand soap, can be considered a liquid herein. A liquid can be a thixotropic liquid. A "semi-solid" as used herein can be a gel, a colloid, or a gum. As used herein, semi-solids and liquids are fluids distinguished on the basis of viscosity: a semi-solid is a high viscosity fluid, while a liquid has lower viscosity. There is no definitive dividing line between these two types of fluids. A semi-solid can, in certain embodiments, have a viscosity as high as thousands of mPa·s. Carriers among those useful herein include liquids, pastes, ointments, and gels, and can be transparent, translucent or opaque.

In certain embodiments, the compositions of the present invention are oral care compositions, suitable for administration to the oral cavity. Such compositions include dentifrices, mouthwashes, mouth rinses, dental gels, lozenges, beads, gums, oral strips, mints, liquid toothpastes, sprays, paint-on gels, lip balms, whitening strips, breath strips, oral chews, and combinations thereof. An oral care composition disclosed herein can be used, for example, for cavity prevention, whitening, plaque prevention or reduction, gingivitis prevention or reduction, tartar control, sensitivity prevention or reduction, or breath malodor prevention or reduction, and stain prevention.

The specific composition of the carrier preferably depends on the intended use of the composition. In various embodiments, the carrier is aqueous, comprising from 5% to 95% water or from 10% to 70% water. In other embodiments, the carrier is substantially non-aqueous. In a dentifrice carrier, water content can be from 5% to 70%, from 10% to 50%, or from 20% to 40%. When the presence of water will cause the film to disintegrate, it is particularly preferred that the dried film contain no free water, in which the amount of water is substantially 0%, or negligible.

The carrier may comprise any of a variety of materials, including emulsifiers, thickeners, fillers, and preservatives. In some embodiments, the carrier may include a functional or active material, such as those described above. In some embodiments, the carrier comprises the same functional material as the film.

In one embodiment, the carrier is suitable for use as a dentifrice. In some embodiments, the carrier comprises a humectant, such as glycerine, sorbitol or an alkylene glycol such as polyethylene glycol or propylene glycol. In some configurations, the carrier comprises a humectant at a level of from 10% to 80% by weight, or 20% to 60% by weight of the composition. Carrier compositions among those useful herein are disclosed in U.S. Pat. No. 5,695,746 to Garlick, Jr., et al., and U.S. Pat. No. 4,839,157 to Mei-King Ng et al.

In various dentifrice embodiments, the carrier comprises thickeners, gelling agents or combinations thereof. Thickeners or gelling agents useful herein include inorganic, natural or synthetic thickeners or gelling agents. In some configurations, the carrier comprises the thickener and gelling agent at total levels of from 0.10% to 15% by weight, or 0.4% to 10% by weight of the composition. Examples of thickeners and gelling agents useful herein include inorganic thickening silicas such as: an amorphous silica, for example Zeodent® 165 (Huber Corporation); Irish moss; iota-carrageenan; gum tragacanth; or polyvinylpyrrolidone. In certain embodiments, the carrier comprises a polishing agent, such as a silica, a calcined alumina, sodium bicarbonate, calcium carbonate, dicalcium phosphate or calcium pyrophosphate. In various embodiments, the carrier can be a visually clear composition.

In various dentifrice embodiments, comprising a visually clear carrier, the composition comprises at least one polishing agent. Polishing agents among those useful herein include collodial silica, such as, for example, Zeodent® 115 (Huber Corporation), and alkali metal aluminosilicate complexes (i.e., a silica comprising alumina). In some configurations, a polishing agent can have a refractive index close to that of a gelling agent combined with water and/or humectant. In various embodiments, the carrier comprises the polishing agent at a level of from 5% to 70% by weight of the composition.

In certain dentifrices, the carrier comprises a surfactant or mixture of surfactants. Surfactants among those useful herein include water-soluble salts of at least one higher fatty acid monoglyceride monosulfate, such as the sodium salt of the monsulfated monoglyceride of hydrogenated coconut oil fatty acids; cocamidopropyl betaine; a higher alkyl sulfate such as sodium lauryl sulfate; an alkyl aryl sulfonate such as sodium dodecyl benzene sulfonate; a higher alkyl sulfoacetate; sodium lauryl sulfoacetate; a higher fatty acid ester of 1,2-dihydroxy propane sulfonate; and a substantially saturated higher aliphatic acyl amides of a lower aliphatic amino carboxylic acid, such as those having 12 to 16 carbons in the fatty acid, alkyl or acyl radicals; and mixtures thereof. Amides can be, for example, N-lauroyl sarcosine, and the sodium, potassium, and ethanolamine salts of N-lauroyl, N-myristoyl, or N-palmitoyl sarcosine. In various embodiments the carrier comprises the surfactant at a level of from 0.3% to 5% by weight of composition, or 0.5% to 3% by weight of composition.

The present invention also provides methods for making a dentifrice carrier. In one embodiment, water and at least one humectant are dispersed in a conventional mixer until a first homogeneous gel phase is formed. A polishing agent is added into the first homogeneous gel phase. The first homogeneous gel phase and the polishing agent are mixed until a second homogeneous gel phase is formed. A thickener, flavorant and surfactants are added to the second homogeneous gel phase. These ingredients are mixed at high speed under vacuum of about 20 to 100 mmHg.

The compositions of the present invention are preferably stable under normal conditions of storage. As referred to herein, "stable" refers to the lack of significant adverse effect on one, and preferably all, compositional attributes such as appearance, flavor, rheology, and chemical composition of the composition. Preferably, stability in the present compositions includes the compositional and physical stability of film (including fragments, if any) in the composition. In various embodiments a composition comprising a film is stable upon storage at ambient temperature for at least about two years. It is understood, however, that in some embodiments, an otherwise stable film can disintegrate during use (as discussed above), for example, during toothbrushing using a dentifrice composition.

In certain embodiments, a composition can comprise, in addition to film fragments as described herein, two or more carriers, each of which contributes a phase to the composition. Such a composition can be stable to color bleeding. For example, a composition can include film fragments and a striped dentifrice such as that disclosed in U.S. Pat. No. 6,315,986 to Wong et al. In certain embodiments, the film fragments can be of different color(s) than the stripe(s) for enhanced aesthetic appeal.

The dentifrice composition conventionally includes thickening agents that provide the dentifrice with the required rheological properties, so that the dentifrice can be stored in a dispensing container over a period of time and thereafter reliably dispensed therefrom by the user. The dentifrice preferably should have the correct viscosity not only to be dispensed but also to exhibit an acceptable consistency within the mouth during tooth brushing. Typical thickening agents include modified celluloses, such as carboxymethyl cellulose (CMC), and other polysaccharide or gum components.

The polysaccharide thickening agent may comprise at least one of xanthan gum and hydroxyethyl cellulose. The polysaccharide thickening agent typically consists of at least one of xanthan gum and hydroxyethyl cellulose. Preferably, the polysaccharide thickening agent consists of xanthan gum which is present in an amount of from 0.1 to 1.5 wt % based on the weight of the composition, preferably from 0.5 to 1 wt % of the composition. However, minor amounts of additional thickeners may be present, for example carrageenan, gum tragacanth, starch, polyvinylpyrollidione, hydroxyethypropyl cellulose, hydroxybutyl methyl cellulose, hydroxypropyl methylcellulose, hydroxyethyl cellulose, sodium carboxymethyl cellulose (sodium CMC) and colloidal silica. In one embodiment, the thickener concentration ranges of 0.1 wt. % to 5 wt. % based on the weight of the composition. In another embodiment, the thickener concentration ranges of 0.5 wt. % to 2 wt. % based on the weight of the composition.

The present invention also provides processes for making compositions comprising a multilayer film entrained in a carrier. In various embodiments, a plurality of fragments of the film matrix of the present invention are combined with a carrier. In some configurations, a carrier and a plurality of multilayer film fragments can be mixed. In some configurations, the mixing can comprise slow stirring. In one preferred embodiment, the process for making the composition comprising a carrier having distributed therein a plurality of lamellar fragments of the multilayer films of the present invention includes:

(a) providing the orally acceptable carrier;
(b) adding lamellar fragments of the multilayer flavored film to the orally acceptable carrier to form a mixture; and
(c) homogenizing the mixture.

The term "homogenizing" as used herein refers to the admixture of the fragments and the carrier so as to attain a substantially homogeneous distribution of fragments in the carrier. It should be noted, however, that the resulting composition still retains two-phase composition characteristics. Homogenizing may be accomplished using any of a variety of conventional homegenizers.

In another method, the film is added to a component of the orally acceptable carrier (e.g., to a humectant for a dentifrice). The remainder of the carrier then may be made, and the mixture of film then added to the carrier.

Certain embodiments described herein also provide methods for administering oral compositions including multilayer films for flavor release to a human or animal subject. As referred to herein, "administering" refers to any method by which a composition is applied on or administered to the subject. In various embodiments, the administration is topical, wherein the composition is applied to an external surface of the subject, such as to a surface of the oral cavity (e.g., teeth, gingival, and tongue). The specific route and method of administration will depend, of course, on the intended use of the composition.

In various embodiments, the present invention provides methods for administering enhanced flavor containing oral compositions to a human or animal subject in need thereof, comprising topically applying to the subject a composition comprising a multilayer film for enhanced flavor release entrained in a carrier. In accordance with this embodiment, the multilayer film is retained on a surface of the oral cavity (e.g., tooth surface or mucosa) after application to provide release of flavor and/or actives contained in the film after initial application. In one embodiment, the method additionally includes disrupting the multilayer film after topically applying the oral composition including the multilayer film. Such disruption may be accomplished by any of a variety of methods, including chemical and/or mechanical means. Chemical means include degradation of the multilayer film by contact with water or a material present at the site of administration (e.g., saliva in an oral care application). Physical means include agitation, grinding, and shear forces produced by application of physical energy to the composition during use (e.g., brushing in a dentifrice application).

In various embodiments, the present invention provides methods for the treatment of an oral care condition. As referred to herein, an "oral care condition" is any disorder or condition which can be prevented or treated by administration of a composition to the oral cavity, including disorders or conditions of the teeth, oral mucosa, gingiva and tongue. Such conditions include caries, gingivitis, periodontitis, and cosmetic conditions such as yellowing and malodour.

The embodiments described herein can be further understood by reference to the following non-limiting examples.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

SPECIFIC EMBODIMENTS OF THE INVENTION

Example 1

This example illustrates a three-layer film containing a flavor containing center layer positioned between two outer surface layers. Each film layer contains HPMC E5 as the film-forming polymer and other excipients also present in the center layer as shown in Table 1 below. The outer surface layers also include HPMC E50 which is used to increase sustained release and the mucoadhesive carbopol 971P which increases the adhesion of the multilayer film to teeth and mucosa of the oral cavity. The center or core layer also includes a flavor.

TABLE 1

| Ingredient | Film Slurry wt. % |
|---|---|
| Surface Layer 1 | |
| Water | 84.80 |
| HPMC E5 | 7.20 |
| HPMC E50 | 1.50 |
| Corn Starch | 2.70 |
| Carbopol 971P | 1.20 |
| Titanium Dioxide | 0.70 |
| Propylene Glycol | 1.40 |
| Tween 80 | 0.50 |
| Center Layer 2 | |
| Water | 77.50 |
| HPMC E5 | 12.30 |
| Corn Starch | 2.20 |

TABLE 1-continued

| Ingredient | Film Slurry wt. % |
|---|---|
| Dsucralase Sweetner | 1.00 |
| Propylene Glycol | 0.60 |
| Flavor | 6.00 |
| Tween 80 | 0.40 |
| Surface Layer 3 | |
| Water | 84.80 |
| HPMC E5 | 7.20 |
| HPMC E50 | 1.50 |
| Corn Starch | 2.70 |
| Carbopol 971P | 1.20 |
| Titanium Dioxide | 0.70 |
| Propylene Glycol | 1.40 |
| Tween 80 | 0.50 |

Layer 1 was cast at 5 mils then dried in a 95° C. oven for 15 minutes. Layer 2 was cast over layer 1 at 15 mils then dried in the same manner. Layer 3 was cast at 5 mils and the final composition dried at 95° C. for another 15 minutes. The thickness of dried film was about 2.75 mils with 1.65 mils for the center flavored layer and 0.55 mils for two surface layers. The film was smashed to pieces by using IKA-WERKE (MF 10 basic). Chips of size between 12 and 20 meshes were collected for making products, such as, for example, tooth paste and mouthwash.

An in-vitro methodology was developed to quantify the binding of film on soft substrate surface. The procedure is summarized bellow.
1. A humectant mixture containing 95% sorbitol and 4% PEG-12 was prepared;
2. 1% test film as obtained above was added to the mixture;
3. The substrate (Vitro-Skin®) was prepared by incubation in clarified saliva for 1 h at 37° C.;
4. The saliva coated substrate was transferred onto a petri dish;
5. The humectant/film mixture was diluted with water (1:1 to 1:2) to mimic the impact of increased salivary flow during brushing, then immediately poured onto the substrate surface;
6. The petri-dish was shaken at 50 rev/min for 5 minutes;
7. The substrate was rinsed with deionized water twice;
8. The film adhered on the substrate surface was evaluated with respect to its binding properties.

In-vitro binding experiment (1:1 dilution) results as shown in FIG. 3 indicated that the layer containing mucoadhesive ingredient Carbopol 971P significantly improved the binding onto saliva coated artificial skin surface.

Example 2

This example illustrates multilayer films having increased binding properties. A multilayer film is prepared as in Example 1 above, except that carbopol 971P is substituted with gelatin. The resulting multilayer film evidences increased adherence to the tooth surface and mucose of the oral cavity.

Example 3

This example illustrates how flavor release is delayed from the multilayer films of this invention. A multilayer film is prepared as in Example 1 or 2 above, except that polyvinyl acetate ("PVA") is added to one of the layers as shown in Table 2 below.

TABLE 2A

| Ingredient - Layer 1 (sticks to surface & release flavor) | |
|---|---|
| Water | 75.50 |
| HPMC E5 | 12.30 |
| Corn Starch | 2.20 |
| Carbopol 971P | 1.20 |
| Green pigment | 0.80 |
| Flavor | 6.00 |
| Sucralose | 1.00 |
| PG | 0.60 |
| Tween 80 | 0.40 |
| Total | 100.00 |
| Ingredient - Layer 2 (delays the release) | |
| Water | 58.70 |
| HPMC E5 | 7.20 |
| HPMC E50 | 1.50 |
| Kollicoat 30D (PVA) | 27.30 |
| Corn Starch | 2.70 |
| TiO2 | 0.70 |
| PG | 1.40 |
| Tween 80 | 0.50 |
| Total | 100.00 |

Following the in vitro method described above this two-layer film was found to bind preferentially on one face only of the two sides (layer 1 only) with surprisingly high selectivity, 80-90% or more.

A simple test was performed in vivo to illustrate the delayed release of this example. The film described in Table 2A above was prepared with a layer 1 thickness of 3.5 mil and a layer 2 thickness of 1.75 mil. Fourteen subjects trained to evaluate sensory aspects of toothpaste and mouthwash participated in this evaluation. Each subject first attached the equivalent weight of film which would be deposited during use to the soft tissue, then immediately brushed with Colgate® MaxFresh® for two minutes. Each parameter was evaluated on a calibrated 15 point scale with 15 being the most intense. As Table 2B illustrates, when film and toothpaste were combined, there was a significant release of flavor, with a peak release from the film at 15 minutes. Similar effects were also observed for Cooling.

TABLE 2B

| Parameter evaluated & timepoint | Colgate® MaxFresh® and Example 3 film | Colgate® MaxFresh® | Difference |
|---|---|---|---|
| Cool - immediate | 12.2 | 11.3 | 0.9 |
| Cool - 1 min | 13.9 | 13.0 | 0.9 |
| Cool - 10 min | 11.4 | 8.6 | 2.8 |
| Cool - 15 min | 10.1 | 6.1 | 4.0 |
| Cool - 20 min | 8.6 | 4.1 | 4.5 |
| Cool - 25 min | 6.7 | 3.2 | 3.5 |
| Cool - 30 min | 5.5 | 3.0 | 2.5 |
| Overall flavor - immediate | 8.6 | 8.0 | 0.6 |
| Overall flavor - 1 min | 7.3 | 6.0 | 1.3 |
| Overall flavor - 10 min | 4.4 | 1.7 | 2.6 |
| Overall flavor - 15 min | 3.7 | 0.4 | 3.3 |
| Overall flavor - 20 min | 2.6 | 0.0 | 2.6 |
| Overall flavor - 25 min | 1.6 | 0.0 | 1.6 |
| Overall flavor - 30 min | 0.7 | 0.0 | 0.7 |

Example 4

This example illustrates how flavor release is delayed from the multilayer films of this invention. A multilayer film is prepared as in Example 1 or 2 above, except that polyvinyl acetate ("PVA") is added to surface layers as 1 and 3 shown in Table 3 below.

TABLE 3

| Surface Layers 1 and 3 | |
|---|---|
| Ingredient | With PVA |
| Water | 75.50 |
| HPMC E5 | 7.20 |
| HPMC E50 | 1.50 |
| Kollicoat 30D (PVA) | 10.00 |
| Corn Starch | 2.00 |
| Carbopol 971P | 1.20 |
| TiO2 | 0.70 |
| PG | 1.40 |
| Tween 80 | 0.50 |
| Total | 100.00 |

The amount of PVA shown in Table 3 is sufficient to reduce the swelling speed of the multilayer film of Example 1 and increase the dissolution time from less than 2 minutes to 10 to 15 minutes.

Example 5

This example illustrates toothpaste formulations. Toothpaste A contained 3-layer flavored chips prepared as in Example 1. Toothpaste B did not contain any flavored chips as shown in Table 4 below.

TABLE 4

| Ingredient Name | Toothpaste A | Toothpaste B |
|---|---|---|
| Polyethylene Glycol 600 | 1.00 | 1.00 |
| Sodium CMC - 40PM | 0.50 | 0.50 |
| Sodium Saccharin | 0.35 | 0.35 |
| Sodium Fluoride | 0.32 | 0.32 |
| Sorbitol (70% solution) | 68.00 | 68.00 |
| Purified Water | 9.27 | 10.07 |
| Pigment Blue# 15 | 0.01 | 0.01 |
| Silica Zeodent 114 | 8.00 | 8.00 |
| Silica Zeodent 165 | 8.00 | 8.00 |
| Flavor | 1.00 | 1.00 |
| Cocoamidopropyl Betaine | 1.25 | 1.25 |
| Sodium Lauryl Sulfate | 1.50 | 1.50 |
| 3-Layer Flavored Chip | 0.80 | — |
| Total | 100.00 | 100.00 |

The flavor release profile of toothpaste A which contained 3-layer flavored chips followed the pattern of FIG. 1. FIG. 1 illustrates the difference between toothpaste A which included 3-layer flavored chips and toothpaste B which did not. It is readily seen that toothpaste A had a higher flavor intensity profile than toothpaste B. Moreover, the flavor signal generated by the flavor released from the multilayer chips of toothpaste A provided a second more intense flavor signal that occurred during brushing after a period of time in which the flavor of the toothpaste was diminished.

With reference to Example 3, toothpaste A which contained 3-layer film flavored chips followed the flavor release profile of FIG. 1. As illustrated in FIG. 1, initially, the flavor release profile of toothpaste A as measured by flavor levels in saliva followed the same release profile as that of conventional toothpaste B, which contained only 1% by weight flavor. After a period of time, for example, after about 30 seconds, as the flavor from the toothpaste A was consumed, the flavor from the 3-layer film flavored chips was released and after an additional period of time, for example, after about 60 seconds, the consumer experienced a burst of flavor due to the release of the 6% by weight flavor from the 3-layer film flavored chips which lasted throughout the entire brushing experience. The burst of flavor released from the 3-layer flavored chips contained in toothpaste A continued after the initial flavor release thus enhancing the flavor delivery throughout the entire brushing experience.

Example 6

This example illustrates mouthwash formulations. 3-layer flavored chips prepared as in Example 4 is added to mouthwash A. Mouthwash B does not contain any chips as shown in Table 5 below.

TABLE 5

| Ingredient Name | Mouthwash A | Mouthwash B |
|---|---|---|
| Purified Water | 70.51 | 71.01 |
| Sorbitol (70% solution) | 15.00 | 15.00 |
| Glycerin | 5.00 | 5.00 |
| Kelcogel CG-LA | 0.05 | 0.05 |
| Sodium Fluoride | 0.05 | 0.05 |
| Anhadrous Disodium Phosphate | 0.05 | 0.05 |
| Ethyl Alcohol | 6.00 | 6.00 |
| Gantrez BF 96 Solution | 1.50 | 1.50 |
| Sodium Methyl Cocoyl Taurate | 0.25 | 0.25 |
| Menthol Levo | 0.05 | 0.05 |
| Sodium Saccharin | 0.02 | 0.02 |
| Triclosan | 0.03 | 0.03 |
| 38% Na$_2$O Caustic Soda | 0.10 | 0.10 |
| 3-Layer Film Chip | 0.50 | — |
| 35% Sodium Lauryl Sulfate | 0.75 | 0.75 |
| Optacool C | 0.03 | 0.03 |
| Flavor | 0.10 | 0.10 |
| FD&C RedNo. 40 | 0.01 | 0.01 |
| Total | 100.00 | 100.00 |

The flavor release profile of mouthwash A which contains 3-layer flavored chips follows the pattern of FIG. 1. Mouthwash A provides the additional delayed flavor signal, while mouthwash B does not.

Example 7

This example illustrates how to control the time of a second flavor signal of a toothpaste A. A multilayer film is prepared as in Example 3 above, except that the thickness of the layer 2 is increased to 4 mils, an amount effective to control the post-use release of flavor to the desired time of 20 minutes.

Example 8

This example illustrates how to prepare a toothpaste A wherein the flavor intensity of a second flavor signal is controlled. In this example, flavored chips from a three-layer film are prepared in accordance with the procedure of Example 1, except that the amount of flavor in the core layer is varied up to about 15%. The higher the flavor content of the core layer the stronger the flavor intensity of the second flavor signal of toothpaste A.

Example 9

This example illustrates how to provide a second flavor signal that is different from the flavor signal of the base toothpaste. Flavored chips from a 3-layer film are prepared in accordance with the procedure of Example 1. The flavored chips are then added to a toothpaste having the composition of toothpaste A of Example 5 except that the flavor of toothpaste A is different from the flavor of the 3-layer flavored chips. Upon brushing with the toothpaste prepared according to this example, the consumer experiences a second flavor signal which is different and more intense from a first flavor signal of the base toothpaste. The second flavor signal is caused by the release of flavor from the 3-layer film chips following a pattern as shown in FIG. 1.

Example 10

This example illustrates how to prepare a toothpaste that can provide a cooling sensation signal in addition to a burst of flavor. Chips from a 3-layer film are prepared as in Example 1 except that the flavor of the center layer is supplemented with a cooling sensation agent such as WS-3. The WS-3 containing flavored chips are then added to a toothpaste having the composition of toothpaste A of Example 5. Upon brushing the consumer feels a cooling sensation in addition to the flavor of toothpaste A and the flavor present in the 3-layer chips contained therein.

Example 11

This example shows how to prepare a toothpaste that can provide a tingling sensation signal in addition to a burst of flavor. Chips from a 3-layer film are prepared as in Example 1 except that the flavor of the center layer is supplemented with a tingling sensation agent such as spilanthol. The spilanthol containing flavored chips are then added to a toothpaste having the composition of toothpaste A of Example 5. Upon brushing a consumer feels a tingling sensation in addition to the flavor of toothpaste A and the flavor present in the 3-layer chips contained therein.

Example 12

This example illustrates how to prepare a toothpaste a sweet sensation signal in addition to a burst of flavor. Chips from a 3-layer film are prepared as in Example 1 except that the flavor of the center layer is supplemented with a sweet sensation agent such as sucralose. The flavored chips also containing a sweet sensation agent are then added to a toothpaste having the composition toothpaste A of Example 5. Upon brushing a customer feels a sweet sensation in addition to the flavor of toothpaste A and the flavor present in the 3-layer chips contained therein.

Example 13

This example shows how to prepare a toothpaste having a warming sensation signal in addition to a burst of flavor. Chips from a three-layer film are prepared as in Example 3 except that the flavor of the center layer is supplemented with a warming sensation agent such as water-activated zeolites The flavored chips also containing a warming sensation agent are then added to a toothpaste having the composition of toothpaste A of Example 5. 10 minutes after brushing, the delay layer dissolves, exposing the zeolite to water from saliva, whereupon the user feels a warming sensation in addition to the flavor released from film layer.

We claim:

1. An oral care composition having enhanced flavor release comprising:
an orally acceptable carrier comprising a first flavor; and
a multilayer substantially lamellar film for extended or delayed flavor release, the multilayer substantially lamellar film including a center layer containing a second flavor, the center layer positioned between two outer surface layers, each outer surface layer including a release modulating agent;
wherein the multilayer substantially lamellar film is adapted to adhere to an oral cavity surface; and
wherein the oral care composition is a dentifrice, mouthwash or oral rinse;
wherein said second flavor is released from said multilayer film at a rate effective to deliver said second flavor to the oral cavity after said multilayer film adheres to an oral cavity surface;
wherein said outer surface layers and said center layer comprise a film forming polymer wherein the film forming polymer is selected from hydroxypropylmethyl cellulose, methyl cellulose, hydroxypropyl cellulose and a combination of two or more thereof;
wherein the release modulating agent is selected from polyvinyl acetate; hydroxypropylmethyl cellulose; and hydroxyethyl cellulose and is present in an amount from about 5% to about 30% by weight of the multilayer film the film forming polymer is present in an amount from about 25% to about 75% by weight of the multilayer film; and the second flavor comprises from about 5% to about 25%, by weight, of the center layer; and
wherein the outer surface layers further comprise a mucoadhesive polymer.

2. The composition of claim 1, wherein said multilayer film further comprises an active material.

3. The composition of claim 1, wherein the outer surface layers comprise the same materials.

4. The composition of claim 1, wherein the mucoadhesive polymer is selected from the group consist of carboxy polymethylene; polycarbophil; and polyvinyl pyrrolidone; and the mucoadhesive polymer is present in an amount from about 1% to about 20% by weight of each outside surface layer.

5. The composition of claim 4, wherein the orally acceptable carrier is a toothpaste or a mouthwash and each outer surface layer has a thickness of from about 0.2 mils to about 4 mils.

6. The composition of claim 1, wherein the center layer further comprises one or more agents selected from the group consisting of a cooling sensation agent, a tingling sensation agent, a sweet signal agent, a warming sensation agent and mixture thereof.

7. The composition of claim 6, wherein the cooling sensation agent is selected from the group consisting of menthol, N-ethyl-p-menthan-3-carboxamide, ethyl-3-(p-menthane-3-carboxamido)acetate, 2-isopropyl-N,2,3-trimethylbutyramide and L-menthyl lactate; the tingling sensation agent is selected from the group consisting of spilanthol, capsaicin, and capsicum oleoresin; the sweet signal agent is selected from the group consisting of sodium saccharin, sucralose, and aspartame; and the warming sensation agent is selected from the group consisting of cinnamic aldehyde, zeolites, and capsaicin.

8. The composition of claim 1, wherein said first flavor is released from said orally acceptable carrier at a rate effective to deliver said first flavor to the oral cavity at about 1 second to about 2 minutes after said composition first contacts the oral cavity surface.

9. The composition of claim 1, wherein said second flavor is released from said center layer at a rate effective to deliver said second flavor to the oral cavity at about 1 minute to about 60 minutes after said composition first contacts the oral cavity surface.

10. The composition of claim 1, wherein said first flavor is released from said orally acceptable carrier and said second flavor is released from said center layer at rates effective to provide maximum flavor intensity at about 2 minutes to about 60 minutes after the contact of said composition with said oral cavity surface.

11. The composition of claim 1, wherein said first flavor is released from said orally acceptable carrier and said second flavor is released from said center layer at rates effective to provide maximum flavor intensity at about 5 minutes to about 30 minutes after the contact of said composition with said oral cavity surface.

12. The composition of claim 1, wherein said first flavor is released from said orally acceptable carrier and said second flavor is released from said center layer at rates effective to provide maximum flavor intensity at about 12 minutes to about 20 minutes after the contact of said composition with said oral cavity surface.

13. The composition of claim 1, wherein said first flavor is released from said orally acceptable carrier and said second flavor is released from said center layer at rates effective to provide maximum flavor intensity at about 10 minutes after the contact of said composition with said oral cavity surface.

\* \* \* \* \*